(12) United States Patent
Takahashi

(10) Patent No.: US 8,648,896 B2
(45) Date of Patent: Feb. 11, 2014

(54) STEREOSCOPIC OPTICAL SYSTEM, AND OPTICAL APPARATUS FOR STEREOSCOPIC MEASUREMENT, STEREOSCOPIC MEASUREMENT APPARATUS AND STEREOSCOPIC OBSERVATION APPARATUS EACH USING THE SAME

(75) Inventor: Susumu Takahashi, Iruma (JP)

(73) Assignee: Olympus Medical Systems Corp., Tokyo (JP)

(*) Notice: Subject to any disclaimer, the term of this patent is extended or adjusted under 35 U.S.C. 154(b) by 917 days.

(21) Appl. No.: 12/653,928

(22) Filed: Dec. 17, 2009

(65) Prior Publication Data

US 2010/0208046 A1 Aug. 19, 2010

(51) Int. Cl.
*H04N 7/18* (2006.01)

(52) U.S. Cl.
USPC ................... 348/49; 348/54; 348/65

(58) Field of Classification Search
USPC .............................. 348/49, 54, 65
See application file for complete search history.

(56) References Cited

U.S. PATENT DOCUMENTS

| | | | |
|---|---|---|---|
| 5,557,454 A * | 9/1996 | Takahashi | 359/378 |
| 6,292,221 B1 * | 9/2001 | Lichtman | 348/345 |
| 2001/0012053 A1 * | 8/2001 | Nakamura | 348/45 |
| 2005/0090743 A1 * | 4/2005 | Kawashima et al. | 600/443 |

FOREIGN PATENT DOCUMENTS

| | | |
|---|---|---|
| JP | 61-080221 | 4/1986 |
| JP | 63-094216 | 4/1988 |
| JP | 04-016812 | 1/1992 |
| JP | 07-261099 | 10/1995 |
| JP | 08-122665 | 5/1996 |
| JP | 08-234117 | 9/1996 |
| JP | 08-304714 | 11/1996 |
| JP | 10-043126 | 2/1998 |
| JP | 10-248807 | 9/1998 |
| JP | 11-006967 | 1/1999 |
| JP | 11-109257 | 4/1999 |
| JP | 2001-108916 | 4/2001 |
| JP | 2001-221961 | 8/2001 |
| JP | 2003-005096 | 1/2003 |

* cited by examiner

*Primary Examiner* — Sath V Perungavoor
*Assistant Examiner* — Jeffery Williams
(74) *Attorney, Agent, or Firm* — Kenyon & Kenyon LLP

(57) ABSTRACT

A stereoscopic optical system includes, at a distal end of an insertion part of an endoscope, a two-path forming optical system for forming two paths of rays involving a parallax, an image forming optical system for forming images out of light travelling along the respective paths of rays in the two-path forming optical system onto a common region, and an image sensor arranged at an image forming position of the image forming optical system. The stereoscopic optical system is further provided with a time-division path switching means that is capable of switching between the two paths of rays in a time-division manner so that only light coming from either one of the two paths of rays formed by the two-path forming optical system enters the image forming optical system.

15 Claims, 11 Drawing Sheets

In    81         82              83

81a 81a    81b  81a       81b

STEREOSCOPIC OPTICAL SYSTEM, AND
OPTICAL APPARATUS FOR STEREOSCOPIC
MEASUREMENT, STEREOSCOPIC
MEASUREMENT APPARATUS AND
STEREOSCOPIC OBSERVATION APPARATUS
EACH USING THE SAME

This application claims benefits of Japanese Patent Application No. 2008-305114 filed in Japan on November 28, the contents of which are hereby incorporated by reference.

BACKGROUND OF THE INVENTION

1) Field of the Invention

The present invention relates to a stereoscopic optical system, and an optical apparatus for stereoscopic measurement, a stereoscopic measurement apparatus and a stereoscopic observation apparatus each using the stereoscopic optical system.

2) Description of Related Art

There grows a request for quantitatively understanding measurement objects such as damages and losses inside machines and affected parts of human bodies. As a technique to measure a measurement object such as a damage or loss or an affected part, there is known the stereoscopic measurement in which an identical point is imaged in two directions involving a parallax, a displacement between corresponding measurement points on the respective images is obtained by a correlation operation between captured images, and the size or depth of the object is measured from the obtained displacement using the principle of triangulation.

Conventionally, as optical systems for capturing images involving a parallax, those recited in, for example, Japanese Patent Kokai No. Hei 08-122665, Japanese Patent Kokai No. 2003-5096, Japanese Patent Kokai No. Hei 11-6967, Japanese Patent Kokai No. Hei 08-234117, and Japanese Patent Kokai No. Hei 07-261099 have been proposed.

The optical system recited in JP Kokai No. Hei 08-122665 is provided at the distal end of the insertion part of an endoscope, and has, for example, an objective optical system 53 composed of negative lenses 51L and 51R arranged side by side and an axially symmetric positive lens unit 52, and two image sensors 54L and 54R arranged side by side, as shown in FIG. 1. In FIG. 1, the reference symbols 52R and 52L denote apertures of diaphragms provided in the positive lens unit 52. It is configured so that optical images 55L and 55R involving a parallax are formed on image pickup surfaces of the image sensors 54L and 54R, upon two paths of rays being formed via the objective optical system 53.

The optical system recited in JP Kokai No. 2003-5096 is used in an endoscope system that includes an objective optical system for conducting measurement or stereoscopic viewing, and is composed of, for example, a first unit 60 with a negative power having two sets of lenses 60L and 60R arranged side by side, a second unit 61 with a positive power, a third unit 62 with a positive power, and an image capture unit 63 including one image sensor 63a, as shown in FIG. 2. It is configured so that two images involving a parallax are formed on that one image sensor 63a via the first unit 60 through the third unit 62.

The optical system recited in JP Kokai No. Hei 11-6967 is provided at the distal end of the insertion part of an endoscope, and has, for example, an objective optical system 74 composed of a pair of negative lenses 71L and 71R, a pair of positive lenses 72L and 72R and one positive lens unit 73, and one image sensor 75, as shown in FIG. 3. It is configured so that two images involving a parallax are formed on that one image sensor 75.

The optical system recited in JP Hei 08-234117 is used in a stereoscopic rigid endoscope, and is composed of, for example, in order from a position of a final image In formed by a relay lens system (not shown), which defines one optical axis and includes at least one relay lens, rearwards, a pupil dividing means 81 arranged in the vicinity of a pupil position, an image forming optical system 82, and one image sensor 83, as shown in FIG. 4A. For the pupil dividing means 81, for example, a rotary disc shown in FIG. 4B having an aperture 81a or a liquid crystal shutter shown in FIG. 4C in which the position of its aperture 81a (81b) is changed is used. It is configured so that two images obtained by pupil division in a time-division manner via the pupil dividing means 81 are captured by the image sensor 83.

The optical system recited in JP Kokai No. Hei 07-261099 is used in a stereoscopic endoscope, and has, for example, an objective optical system 91, relay lens systems 92a, 92b and 92c, a pupil dividing image forming means 93, and image sensors 94R and 94L provided in the grip section of the endoscope, as shown in FIG. 5A. The objective optical system 91 is composed of a pair of front group optical systems $91_1R$ and $91_1L$ arranged in parallel with their optical axes being spaced away by a predetermined distance d and a rear group optical system $91_2$ arranged along a single optical axis, and forms two images 95R and 95L involving a parallax at positions substantially spatially coinciding with each other. The relay optical systems 92a, 92b and 92c are serially arranged to have a common optical axis, and relay the images 95R and 95L at the equal magnification. The pupil dividing image forming means 93 is composed of a pupil image forming lens system 93a, mirror sections 93bR and 93bL, and image forming lens systems 93cR and 93cL. The pupil image forming lens system 93a forms images of two pupils, which are conducted by the relay lens systems 92a, 92b and 92c, of the objective optical system 91 at positions spatially separated from each other. The mirror sections 93bR and 93bL parallel shift two bundles of rays from the two pupils of the objective optical system 91 away from each other. The image forming lens systems 93cR and 93cL are configured to form images 96R and 96L on the image sensors 94R and 94L, respectively.

Also, the optical system recited in JP Kokai No. Hei 07-261099 is configured so that, for example, another occurrence of relay is made on the image side of the relay lens system 92c, by a pupil image forming lens system 93a' and an image forming lens system 93c' that are arranged on the same optical axis as the relay lens system 92c, as shown in FIG. 5B. The relayed images 96R and 96L are formed at a substantially same position, to be captured by an image sensor 94'. A shutter 97 is arranged between the pupil image forming lens system 93a' and the image forming lens system 93c', to intercept the bundles of rays alternately so that two images are not simultaneously formed on the image sensor 94'.

SUMMARY OF THE INVENTION

A stereoscopic optical system according to the present invention is provided with, at a distal end of an insertion part of an endoscope, a two-path forming optical system for forming two paths of rays involving a parallax, an image forming optical system for forming images out of light travelling along the respective paths of rays in the two-path forming optical system onto a common region, and an image sensor arranged at an image forming position of the image forming optical system, and is characterized by being provided with a time-division path switching means that is capable of switching between the two paths of rays in a time-division manner so that only light coming from either one of the two paths of rays formed by the two-path forming optical system enters the image forming optical system.

In the stereoscopic optical system of the present invention, it is preferred that the time-division path switching means is composed of a diaphragm member having two apertures arranged to be mated with the two paths of rays formed by the two-path forming optical system and a blocking member that is capable of blocking the two apertures of the diaphragm member alternately in a time-division manner.

Also, in the stereoscopic optical system of the present invention, it is preferred that the time-division path switching means is composed of two diaphragm members each having an aperture arranged to be mated with each of the two paths of rays formed by the two-path forming optical system and two blocking members that are capable of blocking the apertures of the two diaphragm members alternately in a time-division manner.

Also, in the stereoscopic optical system of the present invention, it is preferred that the diaphragm member is constructed of a variable diaphragm.

Also, in the stereoscopic optical system of the present invention, it is preferred that the time-division path switching means is constructed of a MEMS that has two apertures arranged to be mated with the respective paths of rays formed by the two-path forming optical system and is configured to alternately block the two apertures in a time-division manner.

Also, in the stereoscopic optical system of the present invention, it is preferred that the two-path forming optical system is constructed of a pair of afocal optical systems.

Also, in the stereoscopic optical system of the present invention, it is preferred that the two-path forming optical system is mountably and dismountably arranged.

Also, in the stereoscopic optical system of the present invention, it is preferred that an interpath distance converting means for widening a distance between the two paths of rays involving a parallax is arranged on an object side of the time-division path switching means.

Also, in the stereoscopic optical system of the present invention, it is preferred that the interpath distance converting means is constructed of an axially symmetric wedge prism arranged between the pair of afocal optical systems and the time-division path switching means and that the pair of afocal optical systems are arranged at positions to be mated with the two paths of rays as widened via the axially symmetric wedge prism.

Also, in the stereoscopic optical system of the present invention, it is preferred that the pair of afocal optical systems are decentered as being symmetric with respect to the optical axis of the image forming optical system and in that the interpath distance converting means is constructed of the pair of afocal optical system decentered as being symmetric with respect to the optical axis of the image forming optical system.

Also, in the stereoscopic optical system of the present invention, it is preferred that the two-path forming optical system has a variable focus lens.

Also, in the stereoscopic optical system of the present invention, it is preferred that the two-path forming optical system is constructed of the time-division path switching means.

Also, an optical apparatus for stereoscopic measurement of the present invention is characterized by having the stereoscopic optical system of any one of the above-described inventions.

Also, a stereoscopic measurement apparatus of the present invention is characterized by having a stereoscopic optical system of any of the above-described inventions, a measurement value calculating processing section for calculating, using images of a measurement object which have been captured in the time-division manner through the respective paths of rays via the image sensor of the stereoscopic optical system, a displacement between corresponding measurement points on the respective images by performing a correlation operation and calculating a predetermined measurement value on the measurement object using the displacement as calculated, and a measurement value display means for displaying the measurement value calculated by the measurement value calculating processing section.

Also, in the stereoscopic measurement apparatus of the present invention, it is preferred that an image processing section for performing a predetermined process on the images of the measurement object captured via the image sensor of the stereoscopic optical system and an image display means for displaying an image of the measurement object as image-processed via the image processing section are further included.

Also, in the stereoscopic measurement apparatus of the present invention, it is preferred that a path switching action ordering means for ordering a path switching action by the time-division path switching means and a path switching action control section for controlling the path switching action by the time-division path switching means on the basis of an order from the path switching action ordering means are further included and that the path switching action ordering means is configured to be capable of issuing an order upon selecting either one of a first order mode for performing alternate switching between the paths by the time-division path switching means and a second order mode for performing switching into either one of the paths by the time-division path switching means.

Also, a stereoscopic observation apparatus of the present invention is characterized by having the stereoscopic optical system of any one of the above-described inventions.

Also, in the stereoscopic observation apparatus of the present invention, it is preferred that an image processing section for performing a predetermined process on the images of an observation object captured via the image sensor of the stereoscopic optical system and an image display means for displaying a processed image are further included.

According to the present invention, it is possible to provide a stereoscopic optical system, and an optical apparatus for stereoscopic measurement, a stereoscopic measurement apparatus and a stereoscopic observation apparatus each using the same that are capable of assuring a large parallax, performing measurement or observation on the basis of highly precise image information upon assuring a large image pickup area for the individual images involving a parallax, and performing measurement or observation of an object that is located at a position inaccessible by a linear insertion.

These and other features and advantages of the present invention will become apparent from the following detailed description of the preferred embodiments when taken in conjunction with the accompanying drawings.

DETAILED DESCRIPTION OF THE PREFERRED EMBODIMENTS

Preceding explanation of embodiment modes, the function and effect of the present invention will be explained.

The stereoscopic optical system of the present invention is provided with, at a distal end of an insertion part of an endoscope, a two-path forming optical system for forming two paths of rays involving a parallax, an image forming optical system for forming images out of light travelling along the respective paths of rays in the two-path forming optical system onto a common region, and an image sensor arranged at an image forming position of the image forming optical system.

By forming images out of light travelling through two paths of rays involving a parallax onto a common region to be captured by one image sensor as in the present invention, it is possible to secure a large image pickup area for the respective images involving a parallax.

Also, the configuration in which the two-path forming optical system, the image forming optical system and the image sensor are provided at the distal end of the insertion part of an endoscope allows members arranged behind the distal end of the insertion part to have a flexibility so that the insertion part of the endoscope is flexed. Therefore, it is possible to image a measurement object located at a position inaccessible by linear insertion, in such a case where the measurement object is a curved tube or where an obstacle for measurement exists in front of the measurement object, for example.

Also, the stereoscopic optical system of the present invention is provided with a time-division path switching means that is capable of switching between the two paths of rays in a time-division manner so that only light coming from either one of the two paths of rays formed by the two-path forming optical system enters the image forming optical system.

If a time-division path switching means is provided in this way, individual images involving a parallax can be separately captured by an image sensor. If images involving a parallax can be separately captured, it is possible to measure the size or depth of the object using the principle of triangulation by performing a correlation operation between the separately captured images.

In this way, according to the stereoscopic optical system of the present invention, it is possible to assure a large parallax, to perform measurement on the basis of highly precise image information upon assuring a large image pickup area for individual images involving a parallax, and to measure a measurement object located at a position inaccessible by leaner insertion.

First Embodiment Mode

Figure 1:
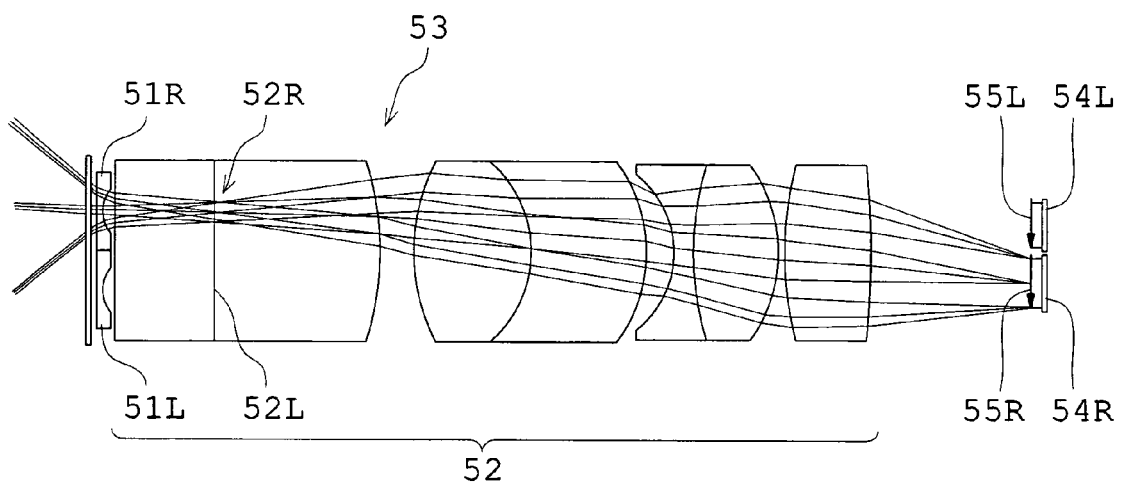
FIG. 1. is an explanatory diagram that shows the schematic configuration of an optical system for capturing images involving a parallax according to one conventional example.
Figure 2:
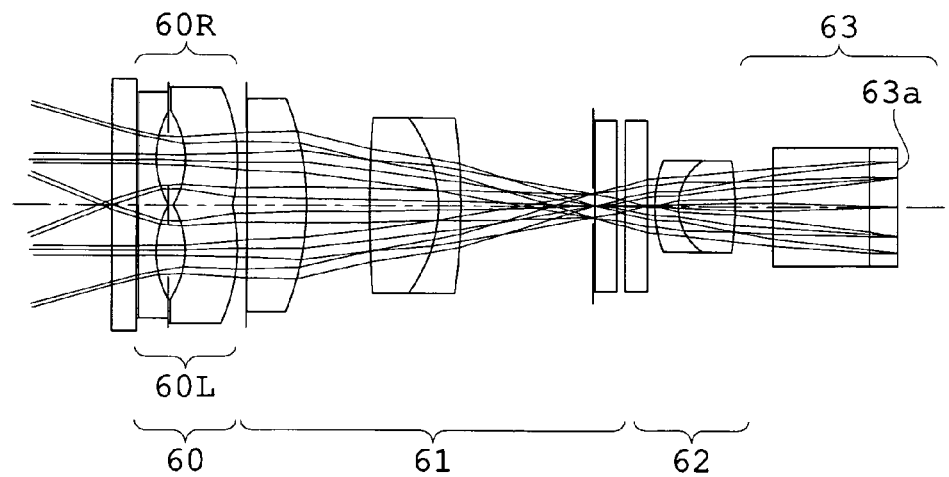
FIG. 2. is an explanatory diagram that shows the schematic configuration of an optical system for capturing images involving a parallax according to another conventional example.
Figure 3:
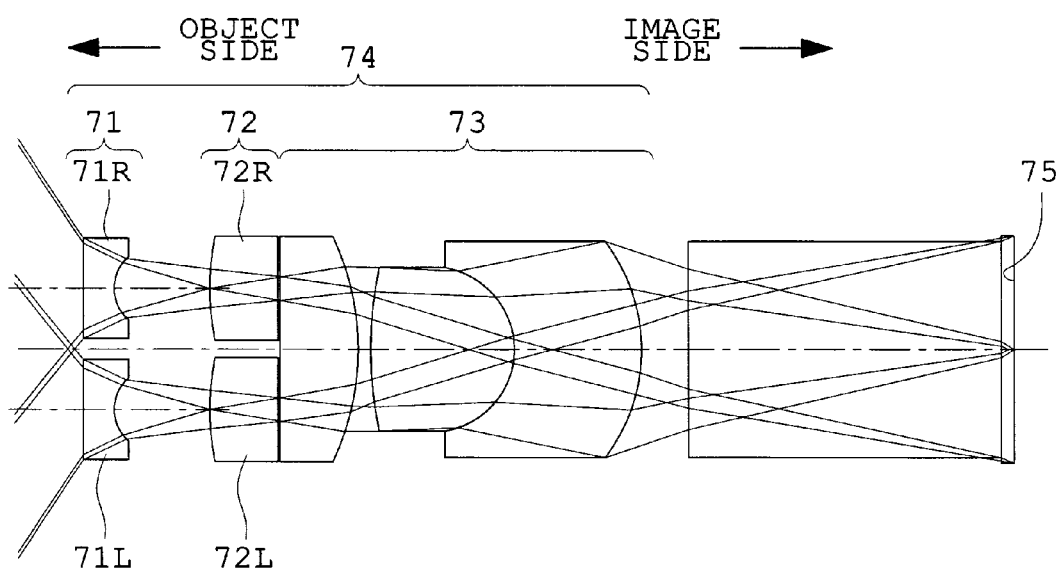
FIG. 3. is an explanatory diagram that shows the schematic configuration of an optical system for capturing images involving a parallax according to still another conventional example.
Figure 4A:
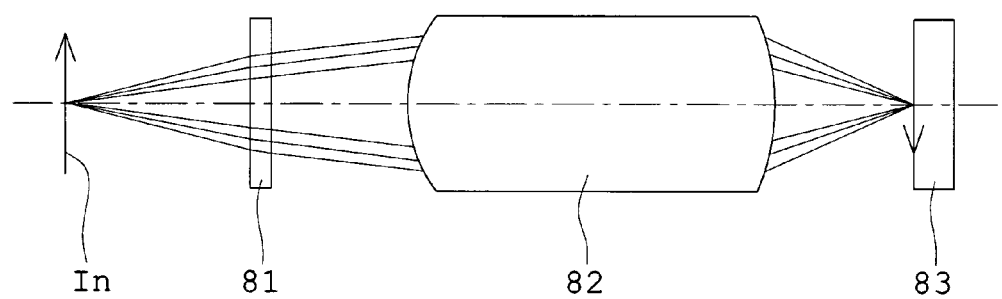
FIGS. 4A, 4B and 4C are explanatory diagrams that show an optical system for capturing images involving a parallax according to still another conventional example, where they are a diagram that shows the schematic configuration, a diagram that shows one example of a pupil dividing means used in the optical system of FIG. 4A and a diagram that shows another example of the pupil dividing means used in the optical system of FIG. 4A, respectively.
Figure 4B:
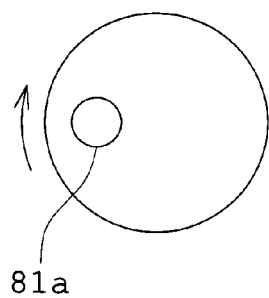
Figure 4C:
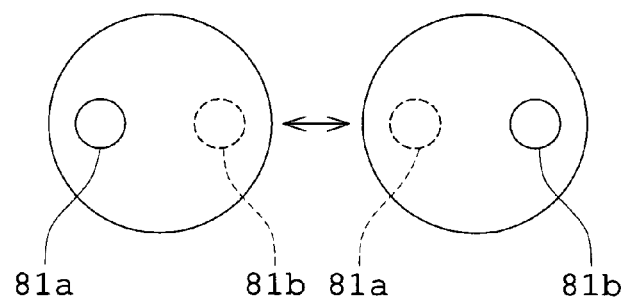
Figure 5A:
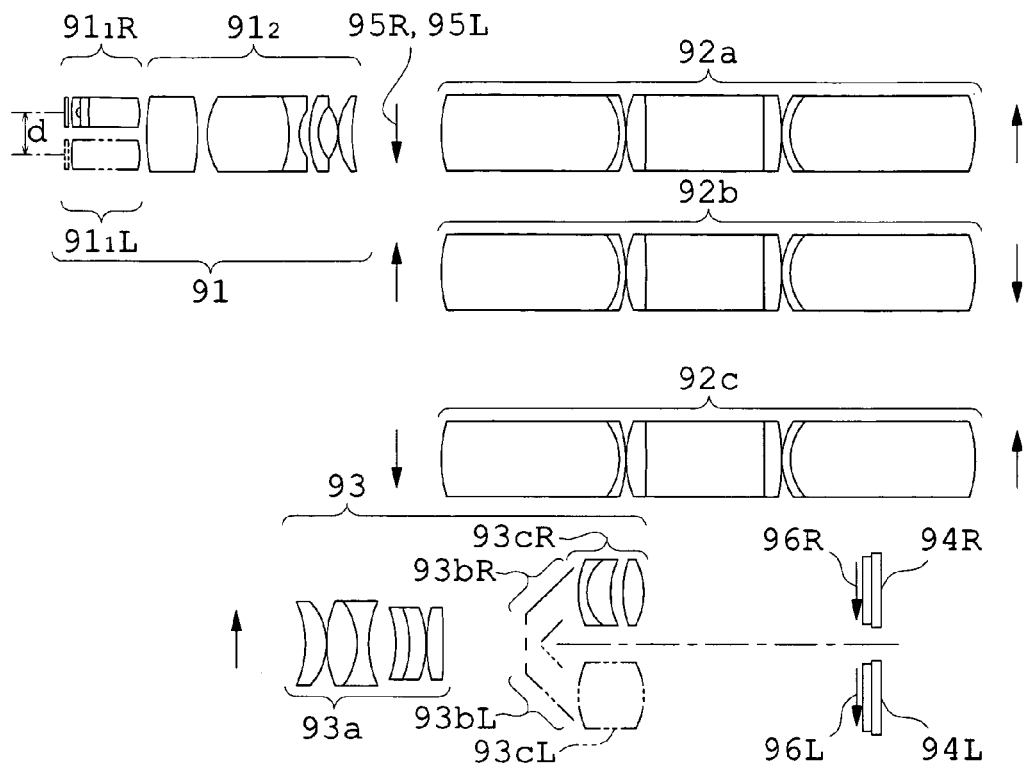
FIGS. 5A and 5B are explanatory diagrams that show an optical system for capturing images involving a parallax according to still another conventional example, where they are a diagram that shows one example of the schematic configuration and a diagram that shows another example of the schematic configuration, respectively.
Figure 5B:
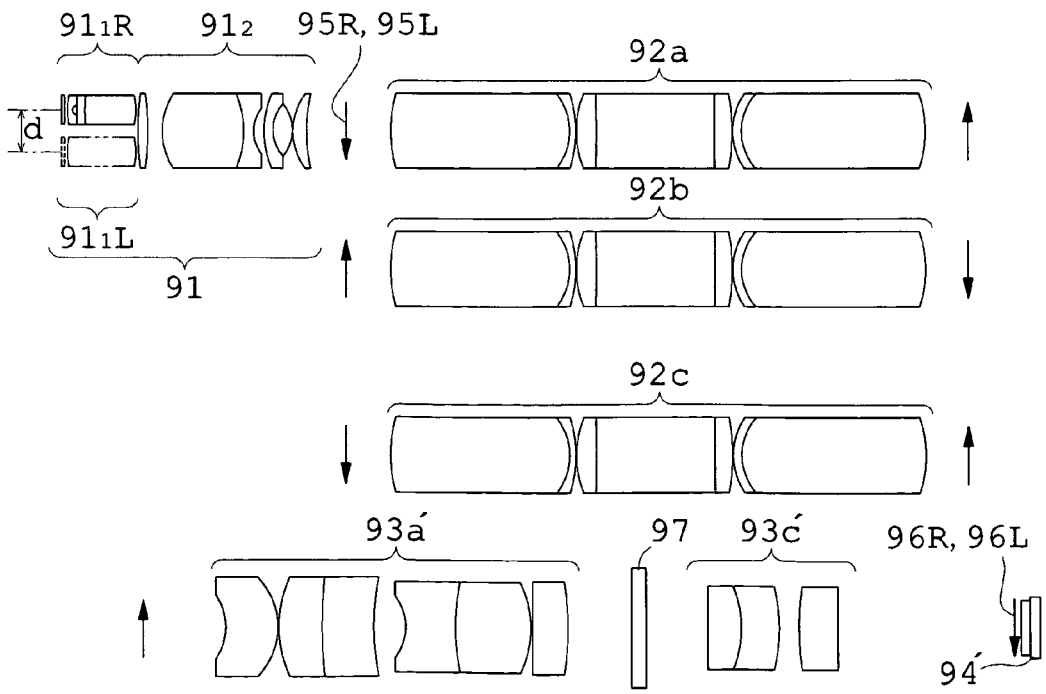
Figure 6:
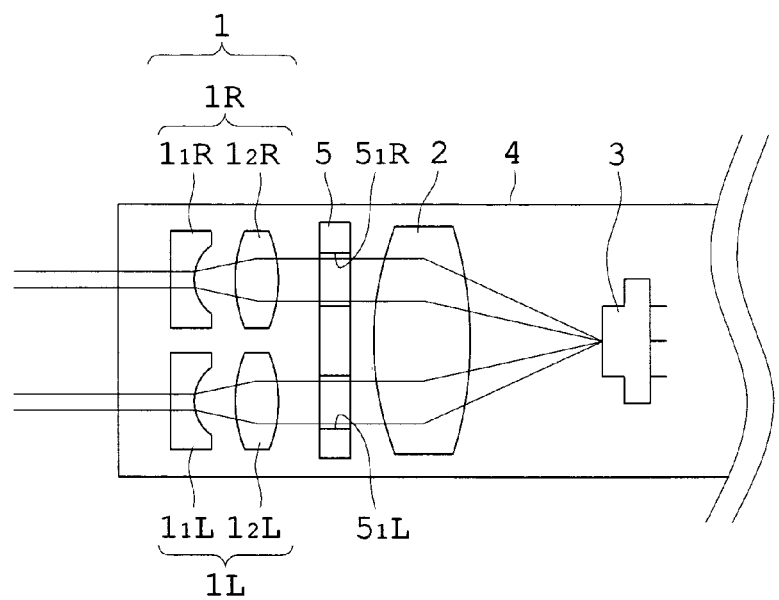
FIG. 6. is an explanatory diagram that shows the schematic configuration of a stereoscopic optical system according to a first embodiment mode of the present invention.
Figure 7A:
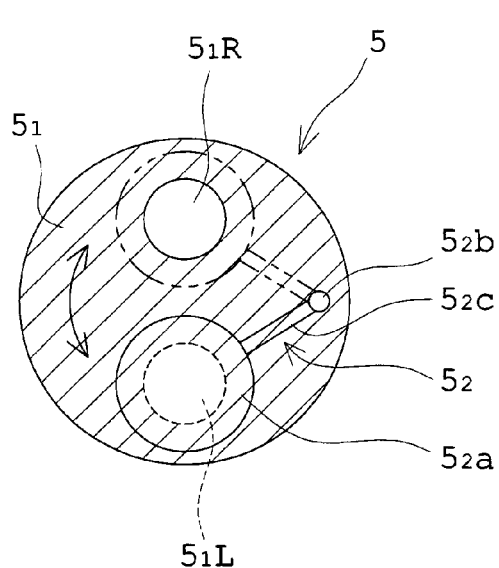
FIGS. 7A and 7B are top plan views that show a time-division path switching means provided for the stereoscopic optical system of FIG. 6, where they are a view that shows one example thereof and a view that shows another example thereof, respectively.
Figure 7B:
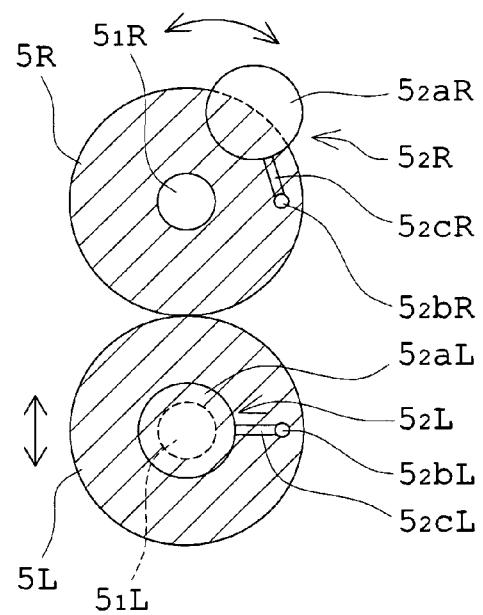

FIG. 6 is an explanatory diagram that shows the schematic configuration of a stereoscopic optical system according to a first embodiment mode of the present invention, and FIG. 7 are top plan views that show a time-division path switching means provided for the stereoscopic optical system of FIG. 6, where FIG. 7A is a view that shows one example thereof and FIG. 7B is a view that shows another example thereof.

The stereoscopic optical system of the first embodiment mode is provided with, at the distal end 4 of the insertion part of an endoscope, a two-path forming optical system 1, one image forming optical system 2, and one image sensor 3.

The two-path forming optical system 1 is composed of a pair of afocal optical systems 1R and 1L axial symmetrically arranged. The afocal optical system 1R(1L) is composed of a concave lens $1_1R(1_1L)$ directing a concave surface toward the image side and a convex lens $1_2R(1_2L)$.

The image forming optical system 2 is configured to form images out of light travelling through respective paths of rays in the pair of afocal optical systems 1R and 1L onto a common region.

The image sensor 3 is arranged at the image forming position of the image forming optical system 2.

Further, the stereoscopic optical system of the first embodiment mode is provided with a time-division path switching means 5 between the two-path forming optical system 1 and the image forming optical system 2.

The time-division path switching means 5 is composed of a diaphragm member $5_1$ and a blocking member $5_2$, as shown in FIG. 7A.

The diaphragm member $5_1$ has two apertures $5_1R$ and $5_1L$ arranged to be mated with two paths of rays provided in the two-path forming optical system 1.

The blocking member $5_2$ is composed of a blocking plate $5_2a$ formed to be capable of blocking the aperture $5_1R$ or the aperture $5_1L$, and a lever $5_2c$ connected with the blocking plate at one end and mounted on the blocking plate $5_2a$ at the other end as being pivotal on a pivot $52b$. The blocking member $5_2$ is connected with a path switching control means not shown, and is configured to turn around the pivot $5_2b$ for blocking the two apertures $5_1R$ and $5_1L$ alternately in a time-division manner via a control signal from the path switching control means.

Whereby, the time-division path switching means 5 is capable of switching between the two paths of rays in a time-division manner so that only light coming from either one of the path of rays enters the image forming optical system.

In the optical system of the first embodiment mode thus configured, light from a measurement object enters the time-division path switching means 5 through the pair of afocal optical system 1R and 1L, and via the time-division path switching means 5, only light from either one of the two paths of rays enters the image forming optical system 2 in a time-division manner. The light entering the image forming optical system 2 from the individual paths of rays is formed as images in a common region on an image pickup surface of the image sensor 4. The image sensor 4 captures the images from the individual paths of rays formed with a time shift.

Here, according to the stereoscopic optical system of the first embodiment mode, since light travelling through the two paths of rays involving a parallax is formed as images on a common region to be captured by the single image sensor 3, it is possible to secure a large image pickup area for the individual images involving a parallax.

Also, since the two-path forming optical system 1, the image forming optical system 2 and the image sensor 3 are provided at the distal end 4 of the insertion part of the endoscope, members arranged behind the distal end of the insertion part are allowed to have a flexibility so that the insertion part of the endoscope is flexed. Therefore, it is possible to image a measurement object located at a position inaccessible by linear insertion, in such a case where the measurement object is a curved tube or where an obstacle for measurement exists in front of the measurement object, for example.

Also, since the time-division path switching means 5, which is capable of switching between the two paths of rays in a time-division manner, is provided so that only light coming from either one of the two paths of rays formed by the two-path forming optical system 1 enters the image forming optical system 2, individual images involving a parallax can be separately captured by the image sensor. As a result of the separate capture of images involving a parallax, it is possible to measure the size or depth of an object using the principle of triangulation by performing a correlation operation between the separately captured images.

In this way, according to the stereoscopic optical system of the first embodiment mode, it is possible to assure a large parallax, to perform measurement on the basis of highly precise image information upon assuring a large image pickup area for individual images involving a parallax, and to measure a measurement object located at a position inaccessible by leaner insertion.

It is noted that the time-division path switching means 5 according to the stereoscopic optical system of the first embodiment mode is allowed to be composed of two diaphragm members 5R and 5L each having an aperture $5_1R$ or $5_1L$ arranged to be mated with the respective paths of rays provided in the two-path forming optical system and two blocking members $5_2R$ and $5_2L$ that are capable of blocking the respective apertures $5_1R$ and $5_1L$ alternately in a time-division manner, as shown in FIG. 7B. In FIG. 7B, the reference symbols $5_2aR$ and $5_2aL$ denote blocking plates, the reference symbols $5_2bR$ and $5_2bL$ denote pivots, and the reference symbols $5_2cR$ and $5_2cL$ denote levers.

Also, while not shown in the drawings, the time-division path switching means 5 is allowed to be a MEMS (Micro Electro Mechanical Systems: a device constructed of mechanical components, sensors, actuators, and electronic circuits integrated on a silicon substrate, a glass substrate or an organic material) that is configured to have two apertures arranged to be mated with the respective paths of rays provided in the two-path forming optical system 1 for blocking the two apertures alternately in a time-division manner.

Also, the pair of afocal optical systems 1R and 1L are allowed to be variable magnification optical systems. Such a configuration makes it possible to achieve optimum measurement in accordance with applications, with a measurement object being enlarged for high precision measurement, reduced for wide range measurement, etc.

Figure 8:
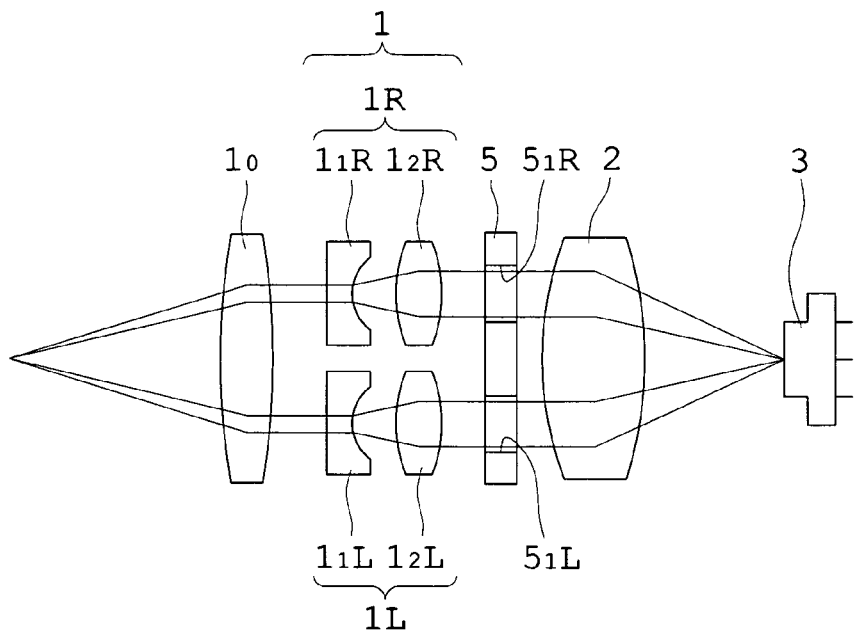
FIG. 8 is an explanatory diagram that shows the schematic configuration of a stereoscopic optical system according to one modification example of the first embodiment mode.

FIG. 8 is an explanatory diagram that shows the schematic configuration of a stereoscopic optical system according to one modification example of the first embodiment mode.

The stereoscopic optical system of the modification example of FIG. 8 is provided with a common convex lens $1_0$ arranged to cover the two paths of rays on the object side of the two-path forming optical system 1 in the optical system of FIG. 6. According to the stereoscopic optical system of the modification example of FIG. 8 thus configured, the function of the convex lens $1_0$ has the effect of widening a range of the object distance at which two images involving a parallax overlap. In addition, it has the effect of focusing on the object surface, also.

Figure 9:
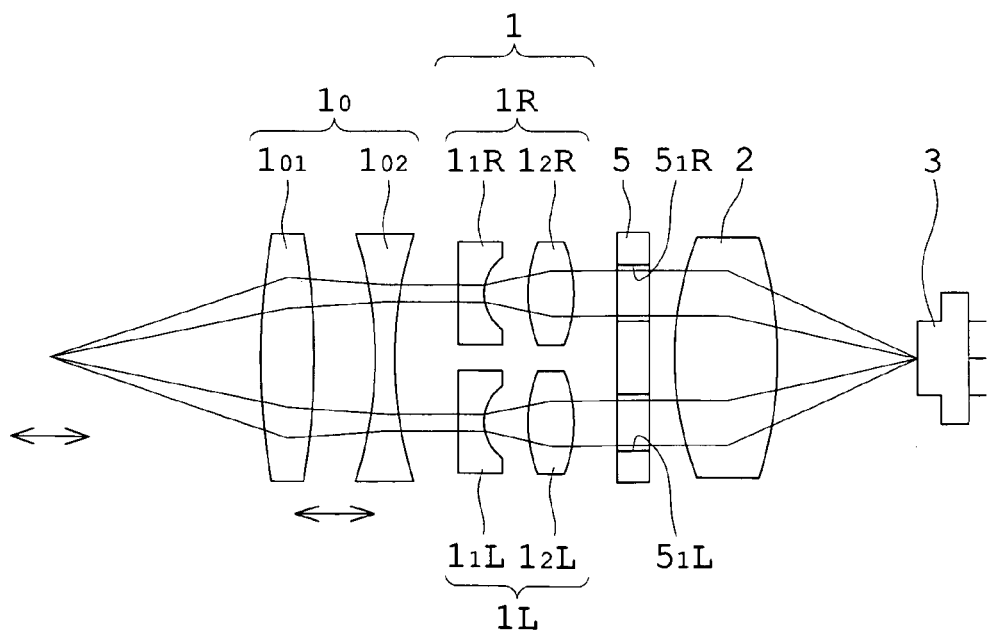
FIG. 9 is an explanatory diagram that shows the schematic configuration of a stereoscopic optical system according to another modification example of the first embodiment mode.

FIG. 9 is an explanatory diagram that shows the schematic configuration of a stereoscopic optical system according to another modification example of the first embodiment mode.

The stereoscopic optical system of the modification example of FIG. 9 is one in which the convex lens $1_0$ in the stereoscopic optical system of the modification example shown in FIG. 8 is composed of a convex lens $1_{01}$ and a concave lens $1_{02}$. The distance between the convex lens $1_{01}$ and the concave lens $1_{02}$ is variable. According to the stereoscopic optical system of the modification example of FIG. 9 thus configured, in addition to the effect of widening a range of the object distance at which two images involving a parallax overlap as in the stereoscopic optical system of the modification example shown in FIG. 8, there is the effect of changing the object distance in focus, for the focal length is changeable. Whereby, the optimum measurement state can be realized.

Second Embodiment Mode

Figure 10A:
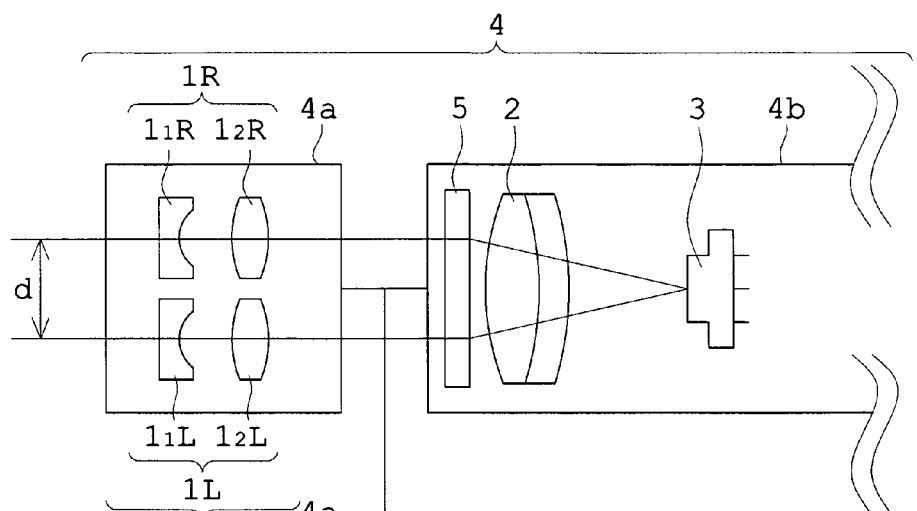
FIGS. 10A, 10B and 10C are explanatory diagrams that show the schematic configuration of a stereoscopic optical system according to a second embodiment mode of the present invention, where they are a diagram that shows the entire configuration including an optical unit for a normal measurement mode, a diagram that shows one example of an optical unit to be mounted on the distal end for a near point measurement, and a diagram that shows one example of an optical unit to be mounted on the distal end for a far point measurement, respectively.
Figure 10B:
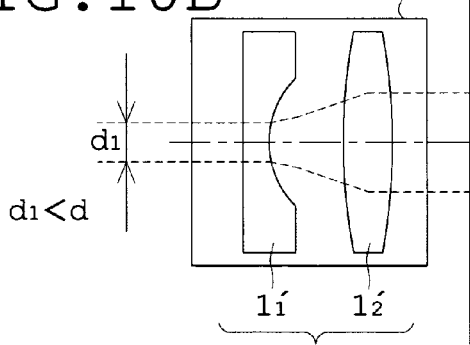
Figure 10C:
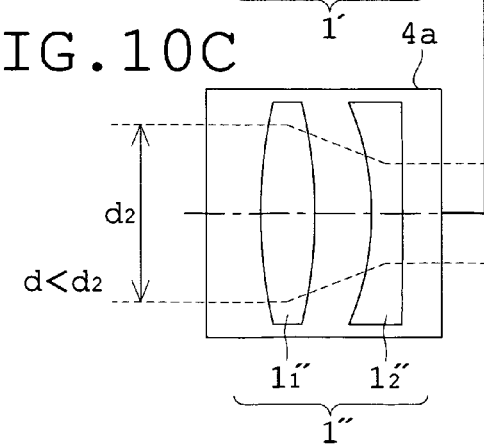

FIG. 10 are explanatory diagrams that show the schematic configuration of a stereoscopic optical system according to a second embodiment mode of the present invention, where FIG. 10A is a diagram that shows the entire configuration including an optical unit for a normal measurement mode, FIG. 10B is a diagram that shows one example of an optical unit to be mounted on the distal end for a near point measurement with a decreased parallax, and FIG. 10C is a diagram that shows one example of an optical unit to be mounted on the distal end for a far point measurement with an increased parallax.

The stereoscopic optical system of the second embodiment mode is such that the two-path forming optical system 1 is configured to be mountable and dismountable on the distal end 4 of the insertion part of an endoscope, as shown in FIG. 10A.

To be specific, the distal end 4 of the insertion part of the endoscope is composed of a distal end exchange portion 4a and a distal end body portion 4b.

The distal end exchange portion 4a is provided with the two-path forming optical system 1. The distal end body portion 4b is provided with the time-division path switching means 5, the image forming optical system 2 and the image sensor 3. The image forming optical system 2 is composed of a cemented lens.

The distal end exchange portion 4a is configured to be mountable and dismountable on and from the distal end body portion 4b.

The other configurations are substantially the same as the stereoscopic optical system of the first embodiment mode.

In a case where images involving a parallax are to be obtained over the entire image pickup region, use of the two-path forming optical system 1 shown in FIG. 10A can assure a large parallax. However, a measurement of a near point using the configuration provided with the two-path forming optical system 1 shown in FIG. 10A is impractical because the parallax is too large. In addition, in some measurement applications, there are cases where enlarging the diameter of the distal end does not obstruct the measurement and an observation with a still larger parallax is desired.

Thus, according to the stereoscopic optical system of the second embodiment mode, since the two-path forming optical system is configured to be mountable and dismountable, it is exchangeable for an optical system with an appropriate parallax in accordance with observation applications.

For example, in a case where a near point is observed with a decreased parallax, a distal end exchange portion 4a provided with an optical system 1' as shown in FIG. 10B can be mounted on the distal end body portion 4b.

The optical system 1' shown in FIG. 10B is composed of a concave lens $1_1'$ directing a concave surface toward the image side and a convex lens $1_2'$. Regarding the optical system 1' shown in FIG. 10B, the parallax $d_1$ where it is mounted on the distal end body portion 4b is smaller than the parallax d where the optical system 1 shown in FIG. 10A is mounted on the distal end body portion 4b.

Also, for example, in a case where a far point is observed with an increased parallax, a distal end exchange portion 4a provided with an optical system 1" shown in FIG. 10C can be mounted on the distal end body portion 4b.

The optical system 1" shown in FIG. 10C is composed of a convex lens $1_1"$ and a concave lens $1_2"$ directing a concave surface toward the object side.

Regarding the optical system 1" shown in FIG. 10C, the parallax $d_2$ where it is mounted on the distal end body portion 4b is larger than the parallax d where the optical system 1 shown in FIG. 10A is mounted on the distal end body portion 4b.

The optical system inside the distal end optical section 4a shown in FIG. 10B or FIG. 10C is a single optical system and does not have two optical axes. However, by switching of the paths of rays by the time-division path switching means 5, the pupil is divided in a time-division manner. Therefore, via the image forming optical system 2, images involving a parallax as pupil-divided in a time-division manner are formed on the entire image pickup region of the image sensor 3, so that images appropriate for measurement are obtained.

The other functions and effects are substantially the same as the stereoscopic optical system of the first embodiment mode.

Third Embodiment Mode

Figure 11:
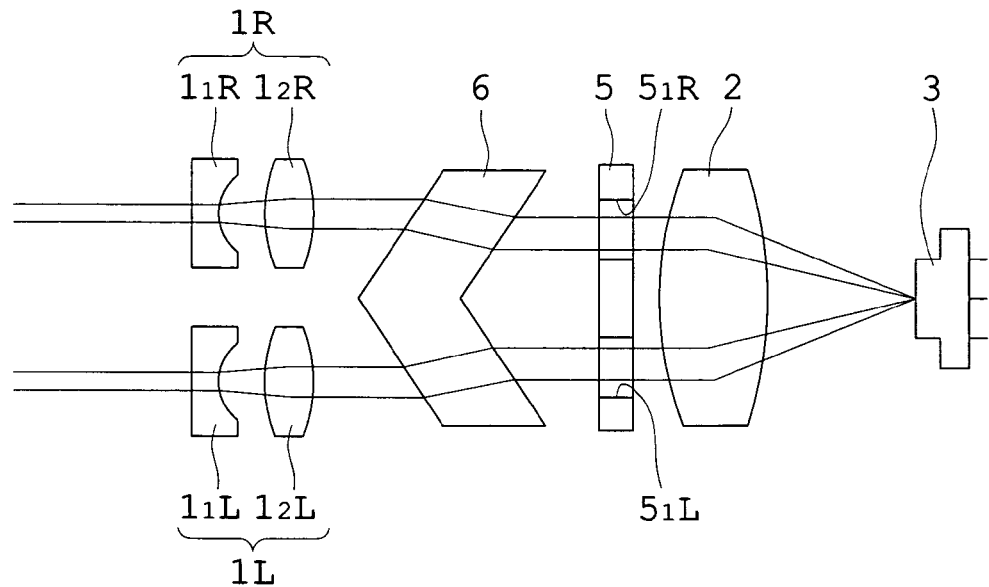
FIG. 11 is an explanatory diagram that shows the schematic configuration of a stereoscopic optical system according to a third embodiment mode of the present invention.

FIG. 11 is an explanatory diagram that shows the schematic configuration of a stereoscopic optical system according to a third embodiment mode of the present invention.

In the stereoscopic optical system of the third embodiment mode, an axially symmetric wedge prism 6 as an interpath distance converting means is provided between the pair of afocal optical systems 1R and 1L as the two-path forming optical system 1 and the time-division path switching means 5. The axially symmetric wedge prism 5 has the function of widening a distance between the two-paths of rays of the time-division path switching means 5. The pair of afocal optical systems 1R and 1L are arranged at positions to be mated with the two paths of rays as widened by the axially symmetric wedge prism 6.

The other configurations are substantially the same as the stereoscopic optical system of the first embodiment mode.

According to the stereoscopic optical system of the third embodiment mode thus configured, a large parallax can be assured.

The other functions and effects are substantially the same as the stereoscopic optical system of the first embodiment mode.

Fourth Embodiment Mode

Figure 12:
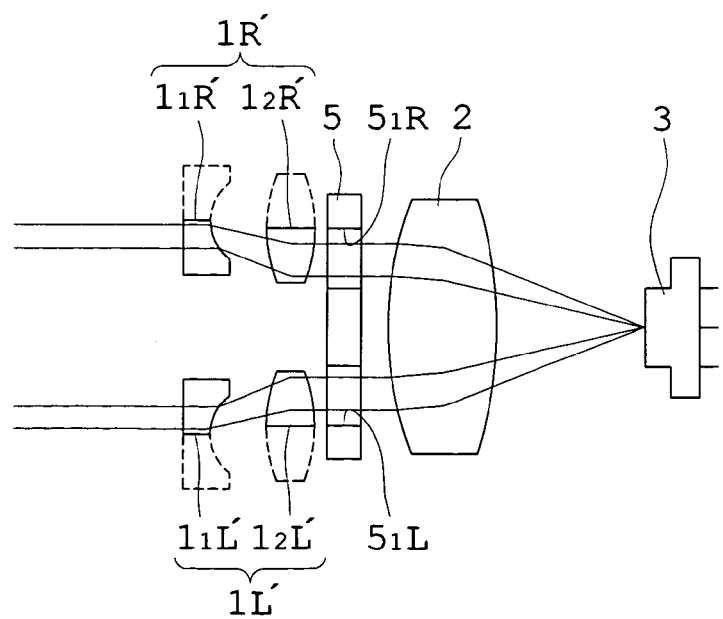
FIG. 12 is an explanatory diagram that shows the schematic configuration of a stereoscopic optical system according to a fourth embodiment mode of the present invention.

FIG. 12 is an explanatory diagram that shows the schematic configuration of a stereoscopic optical system according to a fourth embodiment mode of the present invention.

In the stereoscopic optical system of the fourth embodiment mode, a pair of afocal optical systems 1R' and 1L' as the two-path forming optical system 1 are arranged to be decentered as being symmetric with respect to the optical axis of the stereoscopic optical system, and, as an interpath distance converting means, has the function of widening the distance between the two paths of rays.

The afocal optical system 1R'(1L') is composed of a concave lens $1_1R'(1_1L')$ directing a concave surface toward the image side and a convex lens $1_2R'(1_2L')$. The concave lens $1_1R'(1_1L')$ directing a concave surface toward the image side is constructed of a part inside the optical axis of the concave lens $1_1R(1_1L)$ directing a concave surface toward the image side shown in FIG. 6. The convex lens $1_2R'(1_2L')$ is constructed of a part inside the optical axis of the convex lens $1_2R(1_2L)$ shown in FIG. 6.

The other configurations are substantially the same as the stereoscopic optical system of the first embodiment mode.

According to the stereoscopic optical system of the fourth embodiment mode thus configured, a large parallax can be assured. Furthermore, according to the stereoscopic optical system of the fourth embodiment, since the afocal optical system 1R'(1L') is constructed of parts inside the optical axis of the afocal optical system 1R(1L) shown in FIG. 6, it is possible to assure a large parallax while preventing large-sizing of the diameter of the entire stereoscopic optical system.

The other functions and effects are substantially the same as the stereoscopic optical system of the first embodiment mode.

Fifth Embodiment Mode

Figure 13:
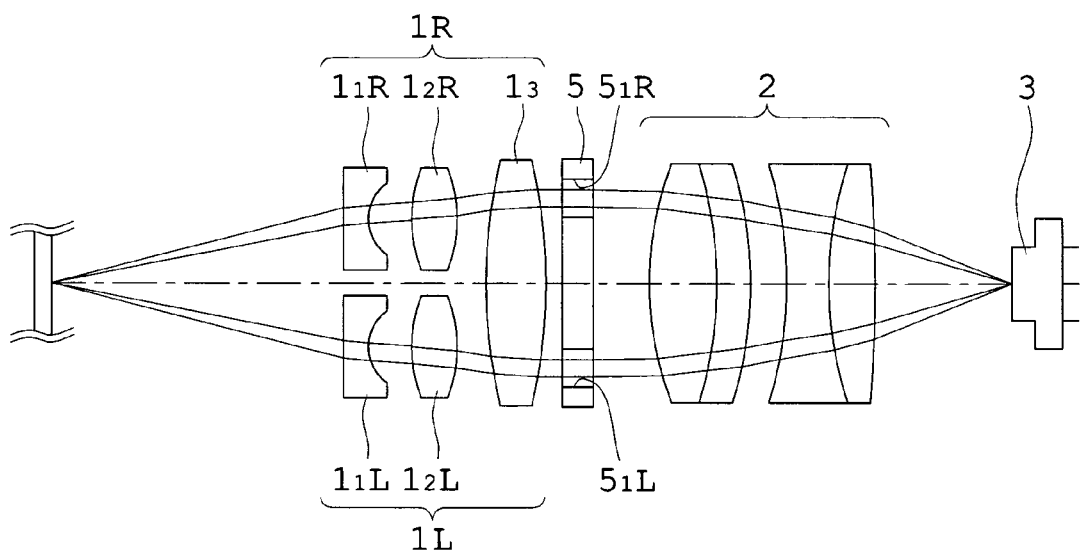
FIG. 13 is an explanatory diagram that shows the schematic configuration of a stereoscopic optical system according to a fifth embodiment mode of the present invention.

FIG. 13 is an explanatory diagram that shows the schematic configuration of a stereoscopic optical system according to a fifth embodiment mode of the present invention.

In the stereoscopic optical system of the fifth embodiment mode, the two-path forming optical system 1 has a variable focus lens $1_3$.

To be specific, in the example of FIG. 13, the two-path forming optical system 1 is composed of a pair of afocal optical systems 1R and 1L, and the afocal optical system 1R(1L) is composed of a concave lens $1_1R(1_1L)$ directing a concave surface toward the image side, a convex lens $1_2R(1_2L)$ and a variable focus lens $1_3$.

The other configurations are substantially the same as the stereoscopic optical system of the first embodiment mode.

According to the stereoscopic optical system of the fifth embodiment mode thus configured, even though the two-path optical system 1 is constructed as an optical system involving a large parallax, focusing onto a near point becomes easy. Therefore, a stereoscopically measurable range can be increased.

The other functions and effects are substantially the same as the stereoscopic optical system of the first embodiment mode.

Although the variable focus lens $1_3$ is arranged on the image side of the convex lens $1_2R(1_2L)$ in the example of FIG. 13, the variable focus lens $1_3$ is allowed to be arranged on the object side of the concave lens $1_1R(1_1L)$.

Sixth Embodiment Mode

Figure 14:
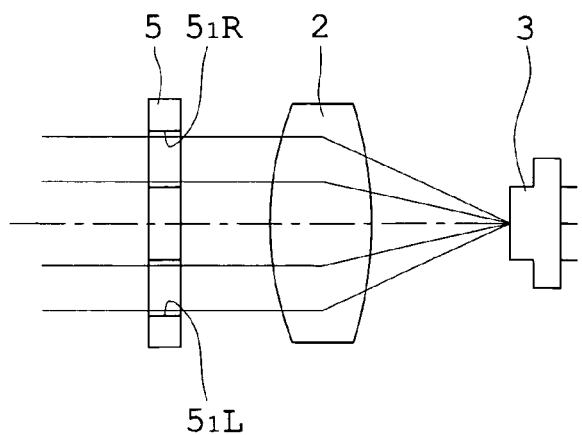
FIG. 14 is an explanatory diagram that shows the schematic configuration of a stereoscopic optical system according to a sixth embodiment mode of the present invention.

FIG. 14 is an explanatory diagram that shows the schematic configuration of a stereoscopic optical system according to a sixth embodiment mode of the present invention.

The stereoscopic optical system of the sixth embodiment mode is composed of a time-division path switching means 5, one image forming optical system 2 and one image sensor 3.

The time-division path switching means 5 has two apertures 51R and 51L arranged to be mated with the respective paths of rays, and forms two paths of rays by blocking the two apertures in a time-division manner via a blocking member (not shown in FIG. 14). Therefore, the time-division path switching means 5 itself is provided with the function as the two-path forming optical system.

The other configurations are substantially the same as the stereoscopic optical system of the first embodiment mode.

The image forming optical system 2 may be composed not of a single lens but of a plurality of lenses.

According to the stereoscopic optical system of the sixth embodiment mode thus configured, since the time-division path switching means 5 is provided with the function as the two-path forming optical system, it is possible to achieve measurement on the basis of highly precise image information upon securing, by a small number of members, a large image pickup area for individual images involving a parallax, and, moreover, it is possible to measure a measurement object that is located at a position inaccessible by a linear insertion.

Next, explanation will be made on embodiment modes of a stereoscopic measurement apparatus using the stereoscopic optical system explained in each of the above-described embodiment modes.

Seventh Embodiment Mode

Figure 15:
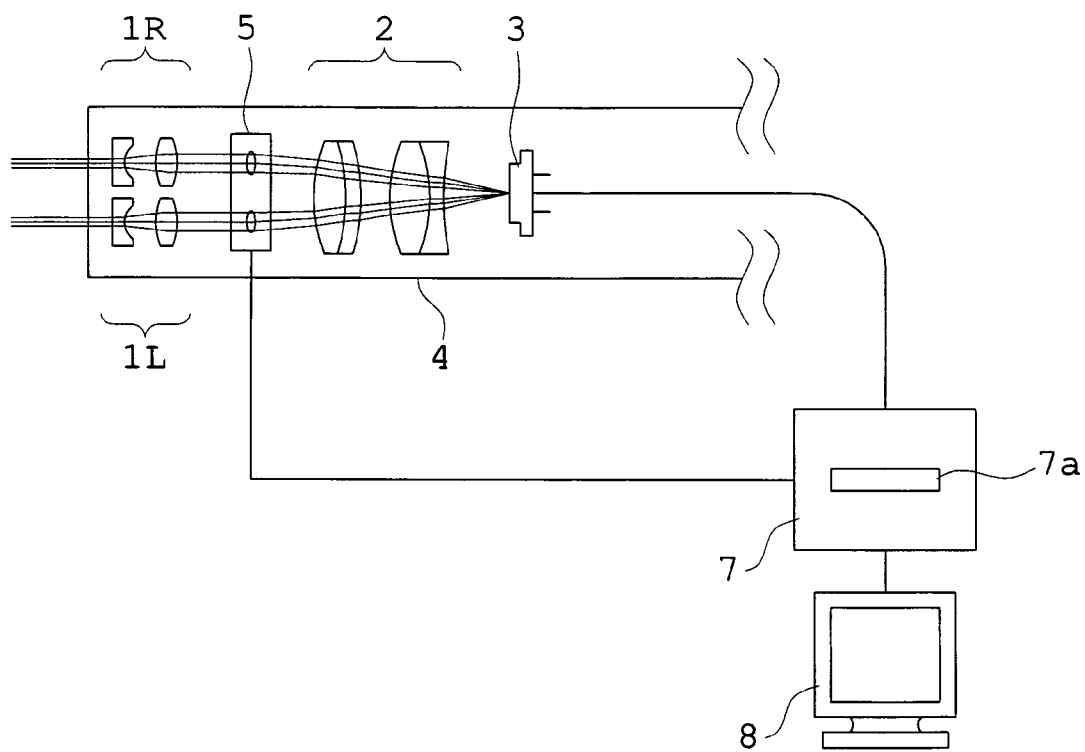
FIG. 15 is an explanatory diagram that shows the schematic configuration of a stereoscopic measurement apparatus using a stereoscopic optical system according to a seventh embodiment mode of the present invention.

FIG. 15 is an explanatory diagram that shows the schematic configuration of a stereoscopic measurement apparatus using a stereoscopic optical system according to a seventh embodiment mode of the present invention.

The stereoscopic measurement apparatus of the seventh embodiment mode is configured to have an endoscope (its entirety not shown) provided with a stereoscopic optical system of any of the first embodiment mode through the sixth embodiment mode shown in FIG. 6 through FIG. 14 at the distal end 4 of the insertion part of the endoscope, a processor 7 and a measurement value display unit 8.

The processor 7 has a measurement value calculating processing section 7a. The measurement value calculating processing section 7a is provided with the function of calculating, using images of a measurement object, which have been captured in the time-division manner through the respective paths of rays via the image sensor 3, a displacement between corresponding measurement points on the respective images by correlation operation and calculating a predetermined measurement value on the measurement object (for example, size or depth of the measurement object) using the displacement as calculated, in association with a path switching action of the time-division path switching means 5.

The measurement value display unit 8 is composed of a monitor for displaying the predetermined measurement value calculated via the measurement value calculating processing section 7a.

In the stereoscopic measurement apparatus of the seventh embodiment mode thus configured, light from the measurement object enters the time-division path switching means 5 through the pair of afocal optical system 1R and 1L, and via the time-division path switching means 5, only light from either one of the two paths of rays enters the image forming optical system 2 in a time-division manner. The light entering the image forming optical system 2 from the individual paths of rays is formed as images in a common region on an image pickup surface of the image sensor 4. The image sensor 4 captures the images from the individual paths of rays formed with a time shift.

Here, in association with the path switching action of the time-division path switching means 5, the measurement value calculating processing section 7a of the processor 7 calculates a predetermined measurement value on the measurement object (for example, size or depth of the measurement object), using images of the measurement object, which have been captured in the time-division manner through the respective paths of rays via the image sensor 3. Then, the measurement value display unit 8 displays the predetermined measurement value calculated via the measurement value calculating processing section 7a.

Eighth Embodiment Mode

Figure 16:
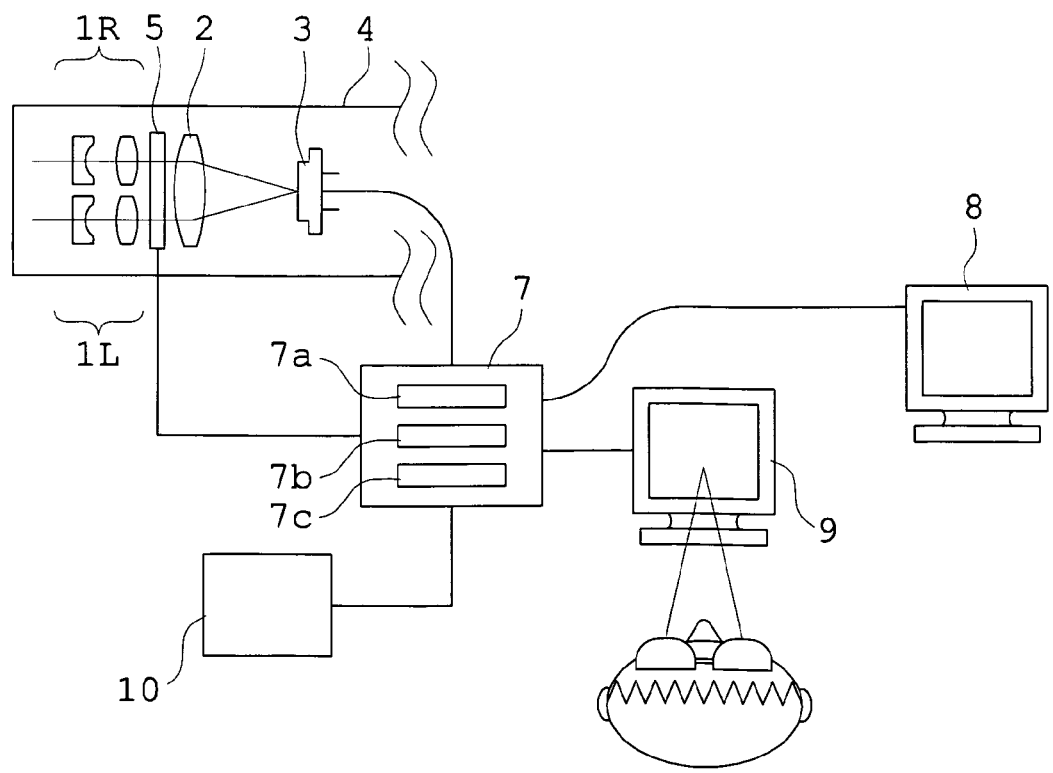
FIG. 16 is an explanatory diagram that shows the schematic configuration of a stereoscopic measurement apparatus using a stereoscopic optical system according to an eighth embodiment mode of the present invention.

FIG. 16 is an explanatory diagram that shows the schematic configuration of a stereoscopic measurement apparatus using a stereoscopic optical system according to an eighth embodiment mode of the present invention.

The stereoscopic measurement apparatus of the eighth embodiment mode is configured to have an endoscope (its entirety not shown) provided with a stereoscopic optical system of any of the first embodiment mode through the sixth embodiment mode shown in FIG. 6 through FIG. 14 at the distal end 4 of the insertion part of the endoscope, a processor 7, a measurement value display unit 8, an image display unit 9, and a path switching action ordering means 10.

The processor 7 has a measurement value calculating processing section 7a, a path switching action control section 7b, and an image processing section 7c.

The measurement value calculating processing section 7a is provided with the function of calculating, in association with a path switching action of the time-division path switching means 5, a predetermined measurement value on a measurement object (for example, size or depth of the measurement object) by correlation operation, using images of the measurement object, which have been captured in the time-division manner through the respective paths of rays via the image sensor 3.

The path switching action control section 7b is provided with the function of controlling the path switching action by the time-division path switching means 5 on the basis of an order from the path switching action ordering means 10.

The image processing section 7c performs the following processing. That is, when a first order mode is issued from the path switching action ordering means 10, it creates a three-dimensional image using image data from the individual paths of rays, which have been divided in the time-division manner via the time-division path switching means 5 and captured by the image sensor 3. Also, when a second order mode is issued from the path switching action ordering means 10, it creates a two-dimensional image using only image data from either one of the paths of rays, into which switching has been made via the time-division path switching means 5 and which have been captured by the image sensor 3.

The measurement value display unit 8 is composed of a monitor for displaying the predetermined measurement value calculated via the measurement value calculating processing section 7a.

The image display means 9 is composed of a monitor for displaying an image of the measurement object as image-processed via the image processing section 7c.

The path switching action ordering means 10 is configured to be capable of issuing an order upon selecting, using a switch, a button or the like of display type on a screen or of mechanical type, either one of the first order mode for successively performing alternate switching between the paths of rays at a regular pitch by the time-division path switching means 5 and the second order mode for performing switching into either one of the paths of rays by the time-division path switching means 5.

In the stereoscopic measurement apparatus of the eighth embodiment mode thus configured, light from the measurement object enters the time-division path switching means 5 through the pair of afocal optical system 1R and 1L.

Here, in a case where two-dimensional image observation on a measurement object is made, an operator sets the path switching action ordering means 10 to the second order mode.

On the occasion of the second order mode being selected, the time-division path switching means 5 is driven to perform switching into either one of the two paths of rays via the path switching action control section 7b. Out of light from the two paths of rays entering the time-division path switching means 5, only light from either one of the paths of rays enters the image forming optical system 2. The light from the one of the paths of rays that enters the image forming optical system 2 is formed as an image on a common region in the image pickup surface of the image sensor 3. Then, the image processing section 7c creates a two-dimensional image using image data from either one of the paths of rays captured by the image sensor 3. Then, the image display means 9 displays an image of the measurement object as image-processed via the image processing section 7c.

Whereby, the operator can observe a two-dimensional image of the measurement object.

On the other hand, in a case where three-dimensional measurement and three-dimensional observation on a measurement object are made, the operator sets the path switching action ordering means 10 to the first order mode.

On the occasion of the first order mode being selected, the time-division path switching means 5 is driven to successively perform alternate switching between the paths of rays at a predetermined pitch via the path switching action control section 7b. Out of light from the two paths of rays entering the time-division path switching means 5, only light from either one of the paths of rays enters the image forming optical system 2. The light from the individual paths of rays that enters the image forming optical system 2 is formed as images on a common region in the image pickup surface of the image sensor 3. The image sensor 3 captures the images from the individual paths of rays formed with a time shift.

Here, in association with the path switching action of the time-division path switching means 5, the measurement value calculating processing section 7a of the processor 7 calculates a predetermined measurement value on the measurement object (for example, size or depth of the measurement object), using images of the measurement object, which have been captured in the time-division manner through the respective paths of rays via the image sensor 3. Then, the measurement value display unit 8 displays the predetermined measurement value calculated via the measurement value calculating processing section 7a.

Also, the image processing section 7c creates a three-dimensional image using image data from the individual paths of rays captured by the image sensor 3. Then, the image display means 9 displays the image of the measurement object as image-processed via the image processing section 7c.

Whereby, the operator is able to obtain a stereoscopic measurement value as well as to observe a three-dimensional image of the measurement object.

Although, in the above configuration, the alternate switching between the paths of rays by the time-division path switching means 5 in a condition where the path switching action ordering means 10 is set to the first order mode is designed to be successively performed at a predetermined pitch, it may be designed to be performed only once.

Alternatively, the configuration may be made so that the pitch and the number of times of the alternate switching between the paths of rays are selectable in setting to the first order mode.

Also, upon constructing the path switching action ordering means 10 as a push button, the configuration may be made so that the second order mode is selected while the push button remains unpushed and the first order mode is selected only while the push button is pushed.

In a case where inspection is made using an industrial endoscope with a priority being given to measurement, it often is true that obtaining two-dimensional images of measurement objects is enough and observation of three-dimensional images results in fatigue of the eyes of an inspector.

Therefore, as described above, if the path switching action ordering means 10 is configured so that the first order mode is selected only while the push button is pushed, it is possible to display a two-dimensional image all the time and to take in the other image by switching, only for an instant, of the paths of rays in a situation where stereoscopic measurement is made. Whereby, fatigue of the eyes of the inspector can be alleviated.

Alternatively, in the stereoscopic measurement apparatus of the eighth embodiment mode, the configuration may be made so that, on the occasion of the first order mode being selected via the path switching action ordering means 10, images of the measurement object travelling through the individual paths of rays and captured in a time-division manner are separately displayed on the image display unit 9 in a two-window display mode.

Alternatively, in the stereoscopic measurement apparatus of the eighth embodiment mode, the configuration may be made so that, on the occasion of the first order mode being selected via the path switching action ordering means 10, images of the measurement object travelling through the individual paths of rays and captured in a time-division manner are alternately displayed at desired intervals on the image display unit 9. In this case, it is preferred that the desired intervals can be separately set.

These configurations also allow two-dimensional images to be displayed all the time, and thus can alleviate fatigue of the eyes of the inspector.

Furthermore, it is preferred to add the following dirt check function using images passing through the individual paths of rays as obtained by switching between the path of rays in a time-division manner in the configuration of the stereoscopic measurement apparatus of the seventh embodiment mode or the eighth embodiment mode.

For example, it is preferred that a dirt check processing section (not shown) is added in the processor 7 and that the dirt check processing section is configured to check, regarding images of a measurement object passing through the individual paths of rays and captured in a time-division manner via the image sensor 3, whether a same figure is captured at a same position, and, if captured, to make a monitor or the like display a caution marker, as there is dust or dirt existing in the optical system for stereoscopic measurement.

For example, if dust or the like is adhered to the image pickup surface of the image sensor, even if the measurement object is imaged, highly accurate measurement cannot be achieved.

Thus, by providing the dirt check function as described above, even if dirt such as dust arises, it can be promptly found and removed, not to obstruct highly accurate measurement.

It is noted that driving of the dirt check function is preferred to be autoactuated on the occasion of actuation of the stereoscopic measurement apparatus. Alternatively, a mode for driving the dirt check function may be added to the path switching action ordering means 10 in the stereoscopic measurement apparatus of the eighth embodiment mode.

Figure 17:
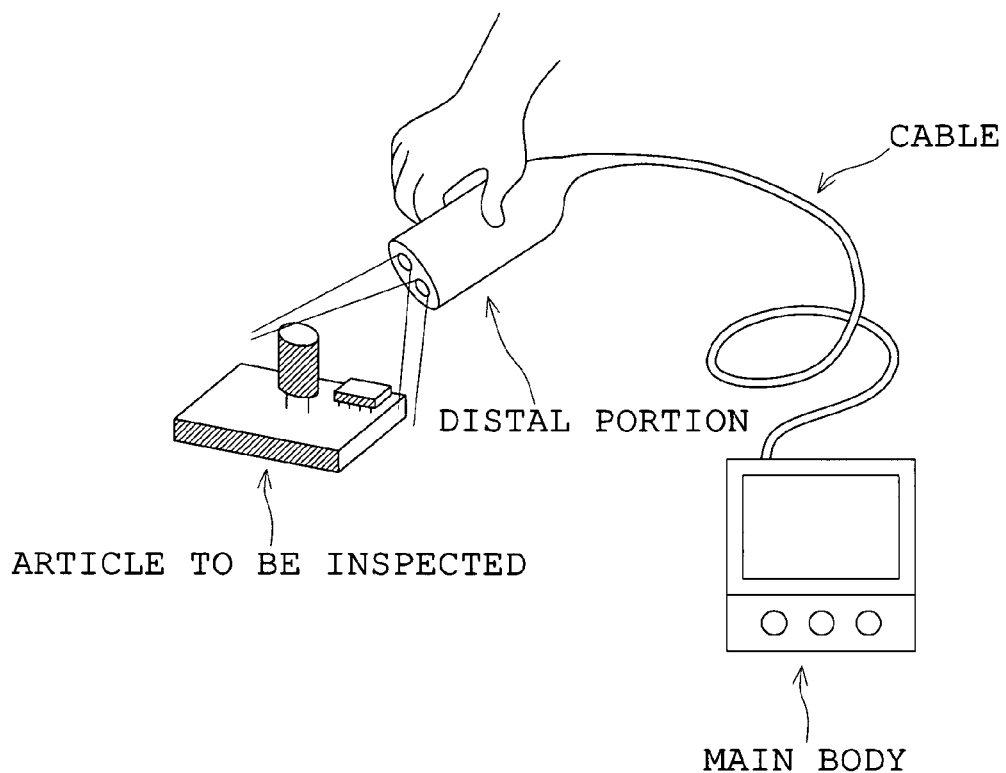
FIG. 17 is an explanatory diagram that shows a hand-held observation apparatus (video microscope), as an example of another apparatus to which the stereoscopic optical system according to the present invention is applicable.
Figure 18:
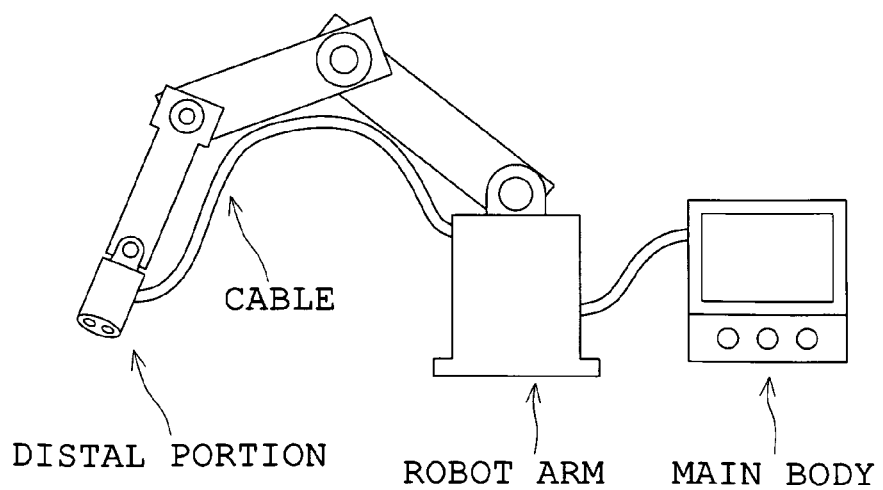
FIG. 18 is an explanatory diagram that shows a sensor having a measurement function, as another example of another apparatus to which the stereoscopic optical system according to the present invention is applicable.

Also, the stereoscopic optical system of the present invention is applicable to those apparatuses such as an observation and measurement apparatus of handheld type (video microscope) as shown in FIG. 17 and a sensor provided with measurement function that is mountable at the distal end of a robot arm as shown in FIG. 18. Application of the stereoscopic optical system of the present invention to such apparatuses makes these apparatuses to be compact and easy to handle, because the stereoscopic optical system of the present invention is small in size.

The explanations above have been made on the embodiment modes of the stereoscopic optical system of the present invention, and of the optical apparatus for stereoscopic measurement, the stereoscopic measurement apparatus and the stereoscopic observation apparatus each using the same. However, the stereoscopic optical system of the present invention and the above-mentioned individual apparatuses are not limited to the configurations of these embodiment modes. For example, characteristic configurations of the individual embodiment modes may be combined together to construct a stereoscopic optical system of the present invention, and an optical apparatus for stereoscopic measurement, a stereoscopic measurement apparatus and a stereoscopic observation apparatus each using the same.

The present invention is useful in industrial and medical fields in which stereoscopic measurement is made for quantitatively understanding measurement objects such as damages and losses inside machines and affected parts of human bodies.

What is claimed is:

1. A stereoscopic optical system comprising, at a distal end of an insertion part of an endoscope:
   a two-path forming optical system for forming two paths of rays involving a parallax;
   an image forming optical system for forming images out of light travelling along the respective paths of rays in the two-path forming optical system onto a common region; and
   an image sensor arranged at an image forming position of the image forming optical system;
   wherein the stereoscopic optical system is provided with a time-division path switching means that is capable of switching between the two paths of rays in a time-division manner so that only light coming from either one of the two paths of rays formed by the two-path forming optical system enters the image forming optical system;
   wherein the time-division path switching means comprises a diaphragm member having two apertures arranged to be mated with the two paths of rays formed by the two-path forming optical system, and a blocking member that is capable of blocking the two apertures of the diaphragm member alternately in a time-division manner; and
   wherein the blocking member includes a blocking plate that is formed to have a size configured to block one of the two apertures of the diaphragm member, and a lever that is connected with the blocking plate at one end and mounted rotatably around a pivot on the diaphragm member at another end, and is configured to cause the blocking plate to block the two apertures alternately by rotating the lever around the pivot.

2. The stereoscopic optical system according to claim 1, wherein the diaphragm member is constructed of a variable diaphragm.

3. The stereoscopic optical system according to claim 1, wherein the two-path forming optical system is constructed of a pair of afocal optical systems.

4. The stereoscopic optical system according to claim 1, wherein the two-path forming optical system is mountably and dismountably arranged.

5. The stereoscopic optical system according to claim 3, wherein an interpath distance converting means for adjusting a distance between the two paths of rays involving a parallax is arranged on an object side of the time-division path switching means.

6. The stereoscopic optical system according to claim 5, wherein the interpath distance converting means is constructed of an axially symmetric wedge prism arranged between the pair of afocal optical systems and the time-division path switching means, and wherein the pair of afocal optical systems are arranged at positions to be mated with the two paths of rays as widened via the axially symmetric wedge prism.

7. The stereoscopic optical system according to claim 5, wherein the pair of afocal optical systems are decentered as being symmetric with respect to an optical axis of the image forming optical system, and wherein the interpath distance converting means is constructed of the pair of afocal optical system decentered as being symmetric with respect to the optical axis of the image forming optical system.

8. The stereoscopic optical system according to claim 1, wherein the two-path forming optical system has a variable focus lens.

9. The stereoscopic optical system according to claim 1, wherein the two-path forming optical system is constructed of the time-division path switching means.

10. An optical apparatus for stereoscopic measurement, comprising the stereoscopic optical system according to claim 1.

11. A stereoscopic measurement apparatus comprising:
the stereoscopic optical system according to claim 1;
a measurement value calculating processing section for calculating, using images of a measurement object, which have been captured in the time-division manner through the respective paths of rays via the image sensor of the stereoscopic optical system, a displacement between corresponding measurement points on the respective images by performing a correlation operation and calculating a predetermined measurement value on the measurement object using the displacement as calculated; and
a measurement value display means for displaying the measurement value calculated by the measurement value calculating processing section.

12. The stereoscopic measurement apparatus according to claim 11, further comprising:
an image processing section for performing a predetermined process on the images of the measurement object captured via the image sensor of the stereoscopic optical system; and
an image display means for displaying the image of the measurement object as image-processed via the image processing section.

13. The stereoscopic measurement apparatus according to claim 12, further comprising:
a path switching action ordering means for ordering a path switching action by the time-division path switching means; and
a path switching action control section for controlling the path switching action by the time-division path switching means on a basis of an order from the path switching action ordering means;
wherein the path switching action ordering means is configured to be capable of issuing an order upon selecting either one of a first order mode for performing alternate switching between the paths of rays by the time-division path switching means and a second order mode for performing switching into either one of the paths of rays by the time-division path switching means.

14. A stereoscopic observation apparatus, comprising the stereoscopic optical system according to claim 1.

15. The stereoscopic observation apparatus according to claim 14, further comprising:
an image processing section for performing a predetermined process on images of an observation object captured via the image sensor of the stereoscopic optical system; and
an image display means for displaying a processed image.

* * * * *